(12) United States Patent
Moon et al.

(10) Patent No.: US 7,839,493 B2
(45) Date of Patent: Nov. 23, 2010

(54) APPARATUS AND METHOD FOR DETECTING PARTICULATES IN WATER

(75) Inventors: Jeon Soo Moon, Daejeon (KR); Kwang Kyu Park, Daejeon (KR); Hee Moon Eum, Daejeon (KR); Kyu Cheol Yeon, Gyeonggi-do (KR)

(73) Assignee: Korea Electric Power Corporation (KR)

( * ) Notice: Subject to any disclaimer, the term of this patent is extended or adjusted under 35 U.S.C. 154(b) by 386 days.

(21) Appl. No.: 11/842,790

(22) Filed: Aug. 21, 2007

(65) Prior Publication Data

US 2009/0051900 A1 Feb. 26, 2009

(51) Int. Cl.
*G01N 21/00* (2006.01)
(52) U.S. Cl. ........................................... 356/72
(58) Field of Classification Search ............... 356/72–73
See application file for complete search history.

(56) References Cited

U.S. PATENT DOCUMENTS 4,982,103 A * 1/1991 Meiffren et al. ........ 250/559.13
6,108,096 A * 8/2000 Ushio et al. .................. 356/432

* cited by examiner

*Primary Examiner*—Tarifur Chowdhury
*Assistant Examiner*—Abdullahi Nur
(74) *Attorney, Agent, or Firm*—Park & Associates IP Law LLC (57) ABSTRACT

Provided is an apparatus and method for measuring a concentration level of particulates in water, by measuring a sound generated upon decomposition of particulates in a water sample which is irradiated by a laser beam. The apparatus comprises a laser beam generator for generating and outputting a laser beam, an output control unit for controlling an output of the laser beam to a constant level by a filter disposed in a laser beam path, a beam splitter for splitting a route of the laser beam output of the output control unit into two routes, a laser beam measurement unit for measuring an output intensity of the laser beam and outputting the measured value as an electrical signal, a condensing lens for condensing the laser beam, a sample cell for storing the water sample and positioned in the laser beam path of the condensed laser beam, a beam stopper for absorbing the condensed laser beam to prevent an external leakage of light, an acoustic sensor coupled with the sample cell for measuring a sound generated from the sample cell, and outputting the measured value as an electrical signal, and a control unit for receiving the signal of the acoustic sensor, calculating the concentration of particulates and outputting a device control signal.

17 Claims, 5 Drawing Sheets

APPARATUS AND METHOD FOR DETECTING PARTICULATES IN WATER

FIELD OF THE INVENTION

The present invention relates to an apparatus and method for measuring a concentration level of particulates in water, by irradiating a laser beam to a sample water for quality analysis, and measuring a sound generated upon decomposition of particulates in the sample by the irradiated laser beam to thereby measure a concentration level of impurity materials in the sample.

BACKGROUND OF THE INVENTION

For determination of a concentration of particulates, such as impurities suspended in water for turbines of thermal power plants, a conventional process involves passing a given amount of water through a filter paper, and measuring an amount of particulates remaining on the filter paper to determine the concentration of particulates. Then, when water has a high concentration of particulates as determined, it is not suitable for turbine water, thereby requiring exchange of turbine water with fresh water.

However, when a method of determining the concentration of particulates is employed using a filter paper, particulate corrosive products in turbine water of the thermal power plant are present at a low concentration, thereby leaving an extremely small amount of particulates on the filter paper. In order to secure a detectable amount of the particulates remaining on the filter paper, it may take a sample collection time of one day or more, and also need an additional time to analyze an amount of the sample remaining on the filter paper even after collection of the sample is complete. As a result, such a method needs much time to determine the concentration of particulates in water of interest and requires an appropriate action in compliance with the thus-determined concentration of particulates, and therefore is pointed out to suffer from problems associated with efficient management of water for thermal power plants.

As another attempt to determine a concentration of particulates in water, a technique for particle-size analysis by a light scattering method has been proposed instead of the method using the filter paper. For technical effectiveness and validity, the conventional particle-size analysis technique using light scattering disadvantageously requires a considerable level of particulates in water, e.g. higher than about 1000 ppm, and can only detect particulates having a particle size of more than 0.02 μm.

SUMMARY OF THE INVENTION

Therefore, the present invention has been made in view of the above problems, and it is an object of the present invention to provide an apparatus and method for determining a concentration of particulates in water, comprising irradiating a laser beam to water for turbines of thermal power plants, detecting an acoustic signal generated upon decomposition of particulates by the irradiated laser beam, and determining a concentration of particulates in turbine water, based on the detection value.

In accordance with an aspect of the present invention, the above and other objects can be accomplished by the provision of an apparatus for determining a concentration of particulates in water, comprising a laser beam generator for generating and outputting a laser beam having a given frequency, an output control unit for controlling an output of the laser beam to a constant level by installation of a filter in a laser beam path of the laser beam generator, a beam splitter for splitting a route of the laser beam output through the output control unit into two routes, a laser beam measurement unit for measuring an output intensity of a portion of laser beam split from the beam splitter and outputting the measured value as an electrical signal, a condensing lens for condensing a portion of laser beam split from the beam splitter, a sample cell for storing analyte water and being positioned in the laser beam path to receive irradiation of condensed laser beam, a beam stopper for absorbing the condensing lens-passed laser beam to prevent leakage of light, an acoustic sensor provided in the sample cell, measuring a sound generated from the sample cell, and outputting the measured value as an electrical signal, and a control unit for receiving the signal of the acoustic sensor, calculating a concentration of particulates and outputting a device control signal.

The output control unit includes a filter for controlling an output of a laser beam, a motor for rotational driving of the filter, and a controller for controlling the motor.

The filter may be any one selected from the group consisting of a variable density filter, a polarization optic and a wedge optic.

The sample cell includes a body having a rectangular shape and storing analyte water as a sample, a cover connected to the upper part of the body and sealing the body, a sample inflow tube installed through the cover and adapted to introduce fresh water into the body, and a sample outflow tube installed through the cover and discharging water in the body to the outside.

The body is made of a transparent optical material capable of transmitting a laser beam while having a high hardness so as to withstand high energy of the laser beam. Examples of the transparent optical material may include BK7, $CaF_2$, $MgF_2$, silica, glass, quartz and the like.

The body is configured to have a rectangular structure such that an irradiating laser beam is not refracted or distorted.

Further, an upper part of the body is provided with a female screw for engaging with the cover, and a lower part of the cover is provided with a male screw for engaging with the body.

The sample inflow tube inside the body is configured to have a longer length than the sample outflow tube.

Further, the sample cell includes a body having a rectangular shape and storing analyte water as a sample, a transparent optical window formed at one side of the body and transmitting a laser beam, a sample inflow tube through-installed at one end of the body and adapted to introduce fresh water into the body, and a sample outflow tube through-installed at one end of the body and discharging water in the body to the outside.

Further, the body is made of any one material selected from a polymer or a metal material.

The laser beam output from the laser beam generator is output in the form of a pulse having a periodicity of 5 to 30 Hz.

The acoustic sensor is installed in a direction perpendicular to an incidence angle of the laser beam.

Further, the acoustic sensor is made in the form of a Piezo Electric Transducer.

The beam stopper is made of ceramic.

The control unit is configured to have a structure that calculates a breakdown ratio (BR) according to the following equation:

BR=Number of Breakdown/Number of Laser Pulses

Further, the control unit is configured to have a structure that calculates a concentration (Y) from the breakdown ratio (BR) according to the following equation:

$$Y = a \times \{BR\}^2 + b \times \{BR\} + c$$

wherein each of a, b and c is a constant.

In the construction of the present invention, water in the sample cell is introduced at a constant flow rate of 10 to 1000 mL/min.

In accordance with another aspect of the present invention, there is provided a method for determining a concentration of particulates in water, comprising providing a given amount of an analyte sample to start an operation, measuring an energy of the generated laser beam, determining whether a laser beam energy within the operation condition is output from the measured laser beam energy, outputting a laser beam pulse when the laser beam energy within the operation condition is output, measuring an acoustic signal, filtering a noise from the measured acoustic signal, detecting a breakdown and then increasing a breakdown number by an increment of +1, determining whether it reaches a measurement period when the laser beam energy within the operation condition is not output, calculating a breakdown ratio and a concentration of particulates when it reaches a measurement period, displaying the calculation results on a screen and storing the results in a memory, and determining whether the measurement continues to proceed and finishing the operation when the measurement does not continue to proceed.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Now, preferred embodiments of the present invention will be described in more detail with reference to accompanying drawings, such that those skilled in the art can easily practice the present invention. These and other objects, advantages and features of the present invention and methods of achieving the same will become apparent from the detailed embodiments given below which are made in conjunction with the following drawings.

It should be understood that the embodiments and the accompanying drawings have been described for illustrative purposes and the present invention is limited only by the following claims. Further, those skilled in the art will appreciate that various modifications, additions and substitutions are allowed without departing from the scope and spirit of the invention as set forth in the accompanying claims.

Figure 1:
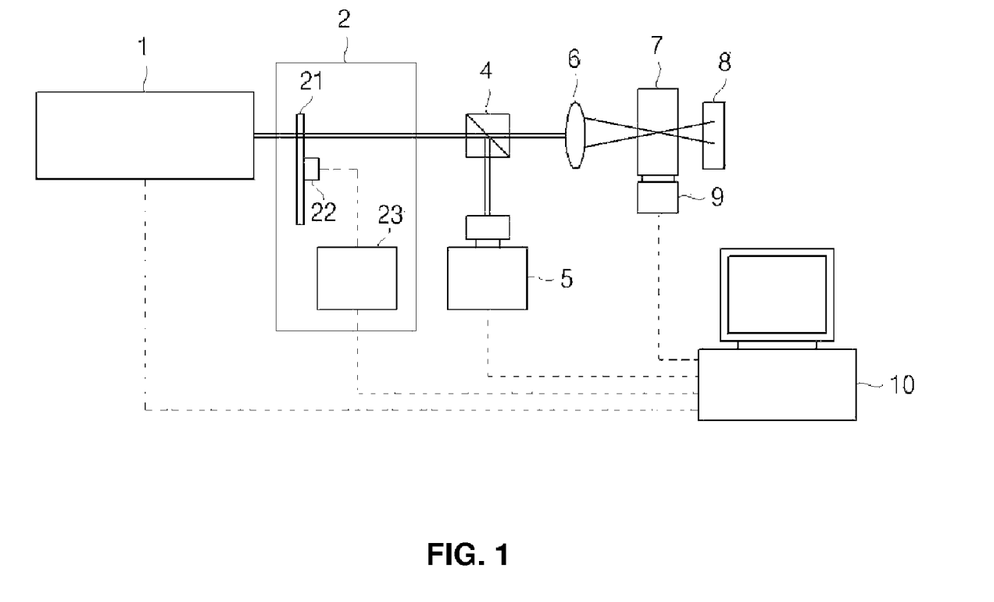
FIG. 1 is a block diagram showing an apparatus for determining a concentration of particulates in water, in accordance with one embodiment of the present invention.

FIG. 1 is a block diagram showing an apparatus for determining a concentration of particulates in water, in accordance with one embodiment of the present invention.

As shown in FIG. 1, an apparatus for determining a concentration of particulates in water in accordance with one embodiment of the present invention includes a laser beam generator 1 for generating and outputting a laser beam having a given frequency, an output control unit 2 installed in a path of the laser beam from the laser beam generator 1 and controlling and transmitting an output of the laser beam to a constant level, a beam splitter 4 for splitting the route of the laser beam output through the output control unit 2 into two routes, a laser beam measurement unit 5 for measuring an output intensity of a portion of laser beam split from the beam splitter 4 and outputting the measured value as an electrical signal, a condensing lens 6 for condensing a portion of laser beam split from the beam splitter 4, a sample cell 7 for storing analyte water and being positioned in the laser beam path to receive irradiation of condensed laser beam, a beam stopper 8 for absorbing the condensing lens-passed laser beam to prevent leakage of light, an acoustic sensor 9 provided in the sample cell 7, measuring a sound generated from the sample cell 7, and outputting the measured value as an electrical signal, and a control unit 10 for receiving the signal of the acoustic sensor 9, calculating a concentration of particulates and outputting a device control signal.

Figure 2:
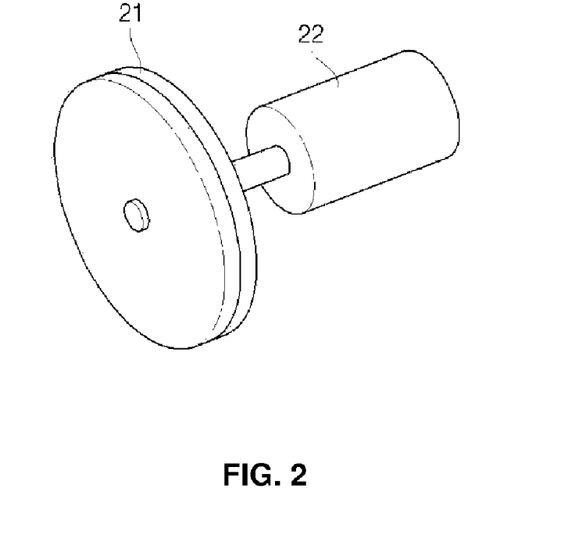
FIG. 2 is a schematic view showing a motor and a filter of an output control unit in an apparatus for determining a concentration of particulates in water, in accordance with one embodiment of the present invention.

FIG. 2 is a schematic view showing a motor and a filter of an output control unit in an apparatus for determining a concentration of particulates in water, in accordance with one embodiment of the present invention.

As shown in FIGS. 1 and 2, the output control unit 2 of the apparatus in accordance with one embodiment of the present invention includes a variable density filter 21 which has a disk shape, rotates about a central axis and has a different density at various positions, a motor 22 for rotating the variable density filter 21, and a controller 23 for controlling the motor 22.

Figure 3:
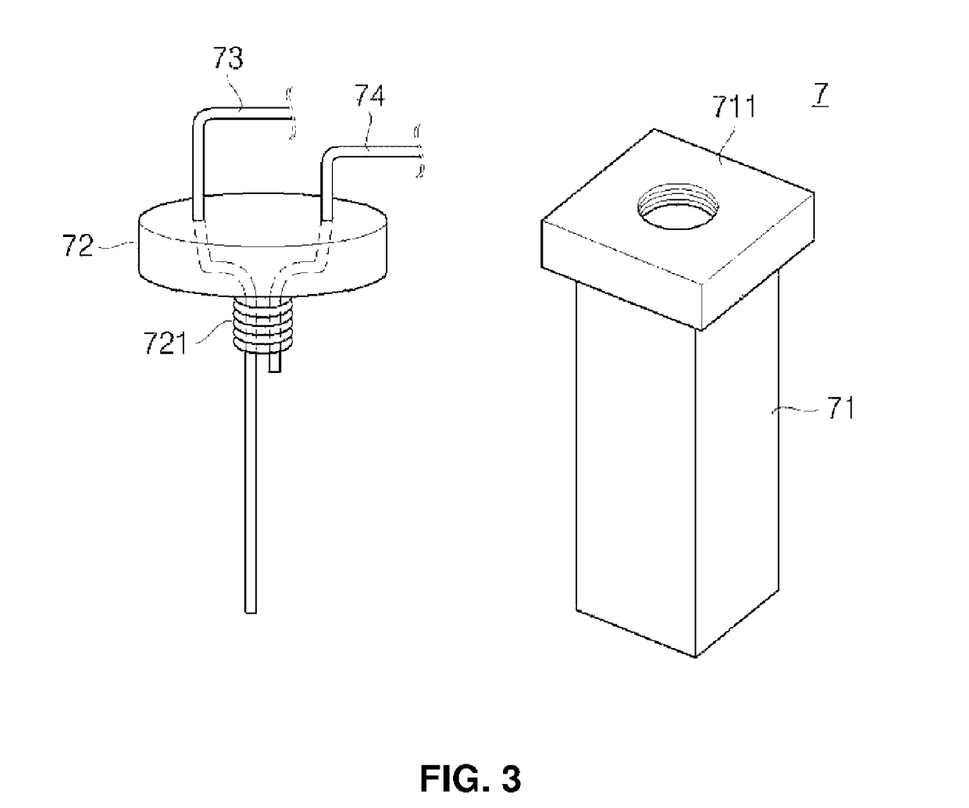
FIG. 3 is a schematic view showing a sample cell in an apparatus for determining a concentration of particulates in water, in accordance with one embodiment of the present invention.

FIG. 3 is a schematic view showing a sample cell in an apparatus for determining a concentration of particulates in water, in accordance with one embodiment of the present invention.

As shown in FIG. 3, the sample cell 7 includes a body 71 having a rectangular shape and storing analyte water as a sample, a cover 72 connected to the upper part of the body 71 and sealing the body 71, a sample inflow tube 73 installed through the cover 72 and adapted to introduce fresh water into the body 71, and a sample outflow tube 74 installed through the cover 72 and discharging water in the body 71 to the outside.

The body 71 is made of a transparent optical material capable of transmitting a laser beam while having a high hardness so as to withstand high energy of the laser beam. Examples of the transparent optical material may include BK7, $CaF_2$, $MgF_2$, silica, glass, quartz and the like. Further, the body 71 has a rectangular structure such that an irradiating laser beam is not refracted or distorted, and an upper part of the body 71 is provided with a female screw 711 for engaging with the cover 72.

The lower part of the cover 72 is provided with a male screw 721 for engaging with the female screw 711 of the body 71.

The sample inflow tube 73 inside the body 71 is configured to have a longer length than the sample outflow tube 74.

Figure 4:
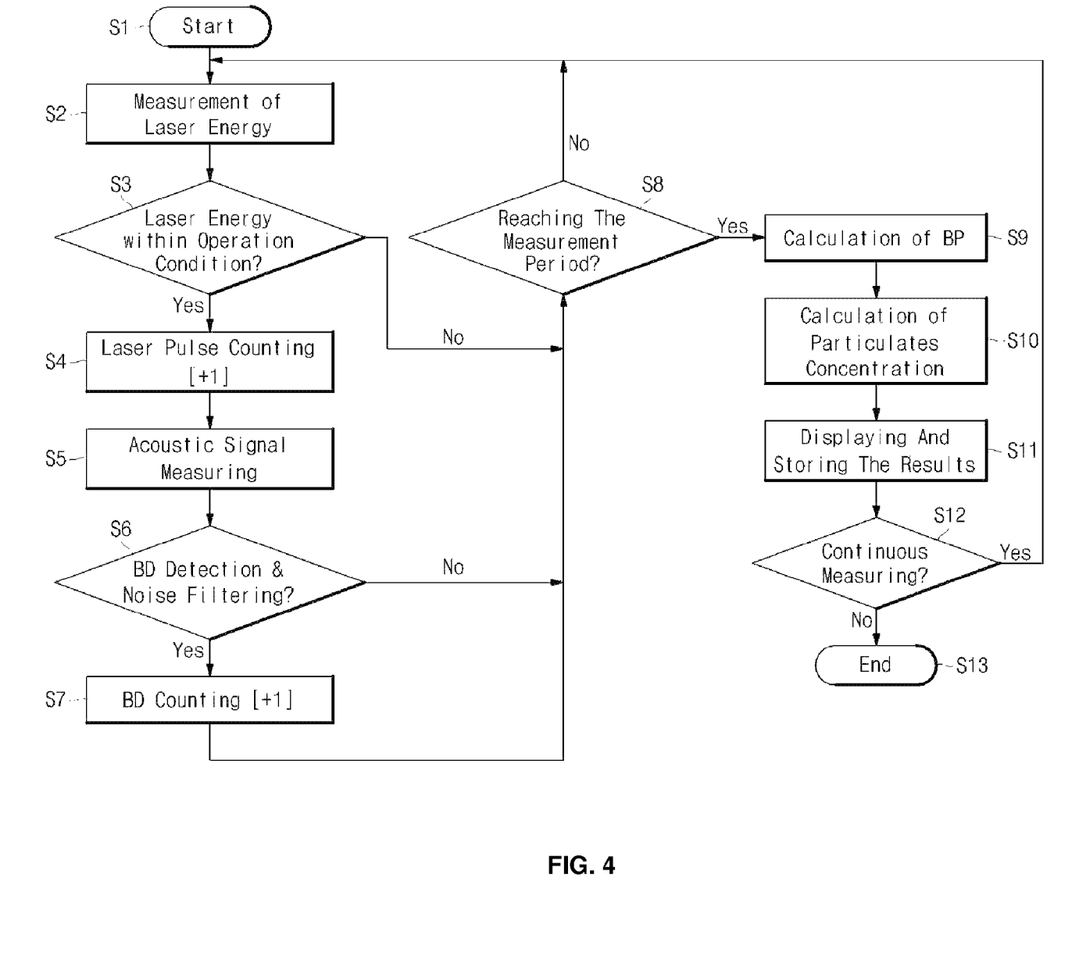
FIG. 4 is an operation flow chart of a method for determining a concentration of particulates in water, in accordance with one embodiment of the present invention.

FIG. 4 is an operation flow chart of a method for determining a concentration of particulates in water, in accordance with one embodiment of the present invention.

As shown in FIG. 4, the method includes providing a given amount of an analyte sample (i.e., water sample) and irradiating a laser beam to start an operation (S1), measuring an energy of the generated laser beam (S2), determining whether a laser beam energy output from the measured laser beam energy is within the operating condition (S3), outputting a laser beam pulse when the laser beam energy output is within the operating condition (S4), measuring an acoustic signal (S5), filtering a noise from the measured acoustic signal and detecting a breakdown number (S6), increasing the breakdown number by an increment of +1 (S7), determining whether it reaches a measurement period when the laser beam energy output is not within the operating condition (S8), calculating a breakdown ratio when it reaches a measurement period (S9), calculating a concentration of particulates (S10), displaying the calculation results on a screen and storing the results in a memory (S11), determining whether the measurement continues to proceed (S12) and finishing the operation when the measurement does not continue to proceed (S13).

Based on the aforementioned construction, functions and effects of the apparatus for determining a concentration of particulates in water in accordance with one embodiment of the present invention will be described hereinafter.

First, an analyte water containing particulates to be analyzed is passed through a sample inflow tube 73 to a transparent sample cell 7. The analyte water sample is introduced at a constant flow rate of 10 to 1000 mL/min. Preferred is a flow rate of 300 to 500 mL/min, which causes substantially no formation of precipitates.

The laser beam output from the laser beam generator 1 passes through the output control unit 2 installed in a path of the laser beam. In the output control unit 2, a disk-shaped variable density filter 21 rotates about a central axis by the motor 22, which leads to changes in a density and consequently changes in the output of the laser beam passing through the variable density filter 21. That is, when the output of the laser beam is weakened by an effect from the outside, a laser beam is allowed to pass through a lower density part of the variable density filter 21, such that an exposure dose of the laser beam is not significantly decreased. On the other hand, when the output of the laser beam is intensified, a laser beam is allowed to pass through a higher density part of the variable density filter 21, such that an exposure dose of the laser beam is not significantly increased. In this manner, the output of the laser beam is maintained at a constant level. Even though the output of the laser beam is dependent upon a structure of the sample cell 7 and an optical material to be used, it is usually maintained in a range of 0.1 to 5.0 mJ.

The laser beam, passed through the variable density filter 21 of the output control unit 2, passes through a beam splitter 4 installed in a path of the laser beam. The beam splitter 4, which is made of a thin coated glass or a prism, splits the laser beam irradiated through the output control unit 2 into two paths, such that the laser beam split into one route is transmitted to a laser beam measurement part 5, and the laser beam split into the other route is transmitted via the condensing lens 6 to the sample cell 7.

The laser beam measurement part 5 is located in the one side path of the laser beam split by the beam splitter 4, measures the output of the irradiated laser beam, and outputs a signal corresponding to the measured value to the control unit 10 as an electrical signal (S2).

The control unit 10 monitors output changes of the laser beam while controlling to constantly maintain the output of the laser beam using the signal input from the laser beam measurement part 5 (S3, S4), and when changes in the output of the laser beam are detected, the control unit 10 transmits a control signal to the output control unit 2. As such, when the control signal is input from the control unit 10, the controller 23 of the output control unit 2 outputs a control signal to a motor 22 to thereby rotate the variable density filter 21, such that the output of the laser beam is always constantly maintained.

Meanwhile, among the laser beam split from the beam splitter 4, the other side path is irradiated to the sample cell 7. At this time, the laser beam, passed through various routes, is dispersed. For efficient laser beam irradiation, the laser beam is thus allowed to pass through the condensing lens 6 composed of a convex lens, for example. As the laser beam passes through the condensing lens 6, the condensed laser beam is irradiated on one point of the sample cell 7.

In the sample cell 7, water for use as the sample is stored in the body 71, and the sample water in the body 71 is discharged through the sample outflow tube 74 to the outside, simultaneously with inflow of fresh water into the body 71 through the sample inflow tube 73. The body 71 of the sample cell 7 is made of a material such as BK7, $CaF_2$, $MgF_2$, silica, glass, quartz or the like, and therefore is capable of transmitting a laser beam while having a high hardness so as to withstand high energy of the laser beam. When the body 71 of the sample cell 7 is formed cylindrically, the irradiated laser beam may be refracted or distorted due to the shape of the body 71. Refraction or distortion of the laser beam is prevented by forming the body 71 into a rectangular shape. An outlet of the sample inflow tube 73 of the sample cell 7 and an inlet of the sample outflow tube 74 are formed at different heights in the body 71. If the outlet of the sample inflow tube 73 and the inlet of the sample outflow tube 74 are formed at the same position, test water introduced through the sample inflow tube 73 may be discharged through the sample outflow tube 74 before the concentration of particulates is determined. Therefore, in order to prevent such a problem, the outlet of the sample inflow tube 73 and the inlet of the sample outflow tube 74 are formed at different heights. The body 71 and cover 72 of the sample cell 7 are engaged and disengaged using a female screw 711 formed on the body 71 and a male screw 721 formed on the cover 72. Therefore, when the inside of the sample cell 7 is contaminated with pollutants, it is possible to easily clean the sample cell 7.

In this manner, when a laser beam is irradiated to test water stored in the body 71 of the sample cell 7, particulates present in water collide with the laser beam and absorb energy of the laser beam. As a result, due to occurrence of thermal ionization and electron excitation in the particulates, particulates decompose into finer particulates resulting in the generation of plasma. In addition, breakdown of the particulates is accompanied by generation of a sound. The sound generated during breakdown of the particulates is measured by the acoustic sensor 9, installed on one side of the sample cell 7, preferably in a direction perpendicular to an incidence angle of the laser beam. The acoustic sensor 9 in the form of a Piezo Electric Transducer outputs the thus-measured acoustic signal to the control unit 10 as an electrical signal (S5-S8).

Instead of using a method of detecting the sound using the acoustic sensor 9, there may be considered to employ a method of detecting plasma using a CCD camera.

Meanwhile, since the laser beam passed through the sample cell 7 still maintains high-power output state, irradiation of such a laser beam to other objects may cause safety concerns. Such a risk is negated by a beam stopper 8 positioned at the rear of the sample cell 7. The beam stopper 8 is preferably made of a material such as ceramic.

After the sound is detected using the acoustic sensor 9, the control unit 10 determines the concentration of particulates in water using the signal input from the acoustic sensor 9 by statistical analysis at an interval of 0.5 to 30 min, according to the following manner.

First, the control unit 10 calculates a breakdown ratio (BR).

The breakdown ratio (BR) is calculated according to the following equation:

BR=Number of Breakdown/Number of Laser Pulses

The breakdown probability (BP), which is expressed in terms of percentage of BR, is calculated according to the following equation:

BP=BR×100(%)

Further, a concentration (Y) is calculated from the breakdown ratio (BR), according to the following equation (S10):

$Y=a\times\{BR\}^2+b\times\{BR\}+c$ wherein each of a, b and c is a constant.

According to the above equation, the breakdown probability (BP) can be calculated from a ratio (BR) of acoustic signal generation frequency to a laser pulse number introduced into the sample cell 7, and a concentration (Y) can be calculated from the thus-obtained breakdown probability (BP).

Figure 5:
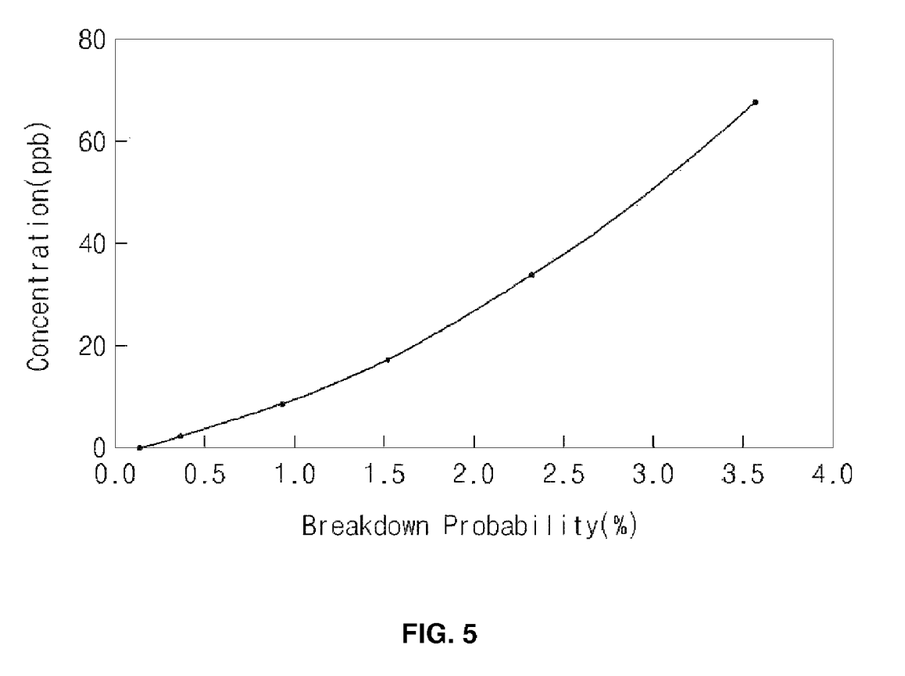
FIG. 5 is a graph showing a concentration (Y) versus a breakdown probability (BP) of an apparatus for determining a concentration of particulates in water, in accordance with one embodiment of the present invention.

FIG. 5 is a graph showing a concentration (Y) versus a breakdown probability (BP) of an apparatus for determining a concentration of particulates in water, in accordance with one embodiment of the present invention, and the concentration (Y) is calculated according to the following secondary equation.

$Y=3.59x^2+6.223x-0.566$ wherein x represents BP.

Next, the control unit 10 displays the calculation results on a screen and stores the results in a memory (S11), determines whether the measurement continues to proceed (S12) and finishes the operation when the measurement does not continue to proceed (S13).

Therefore, it is possible to achieve real-time determination of a concentration of particulates in water, by irradiating laser beam to water for turbines of thermal power plants, detecting an acoustic signal generated upon decomposition of particulates by the irradiated laser beam, and determining a concentration of particulates in turbine water, based on a detection value.

Figure 6:
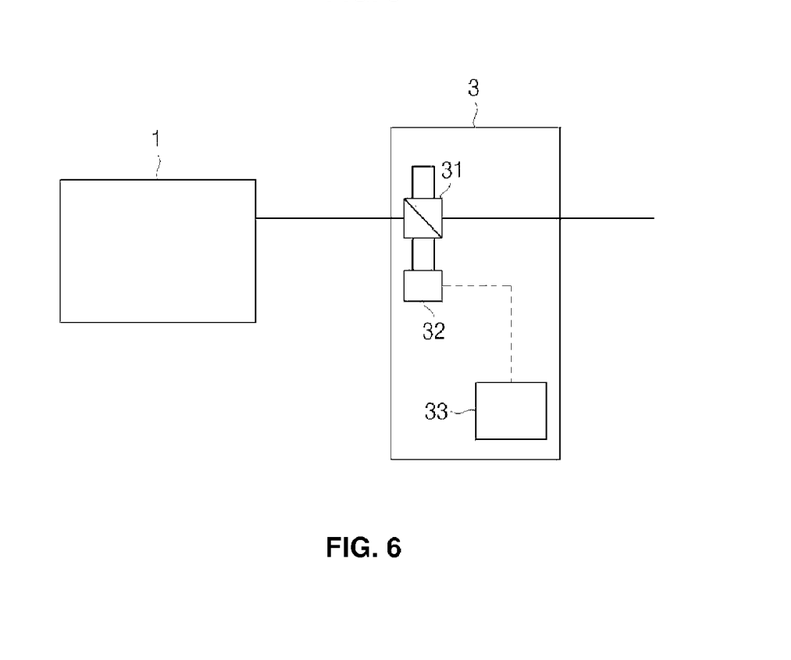
FIG. 6 is a schematic view showing an output control unit of an apparatus for determining a concentration of particulates in water, in accordance with another embodiment of the present invention.

FIG. 6 is a schematic view showing an output control unit of an apparatus for determining a concentration of particulates in water, in accordance with another embodiment of the present invention.

As shown in FIG. 6, an output control unit 3 of the apparatus in accordance with another embodiment of the present invention includes a polarization optic 31, a motor 32 for rotational driving of the polarization optic 31, and a controller 33 for controlling the motor 32.

The polarization optic 31 of the output control unit 3 is intended for high-power energy. As such, the variable density filter 21 may be used when the laser beam energy is relatively low, but the polarization optic 31 should be employed when the laser beam energy is relatively high.

Preferably, the wedge optic may be used instead of the polarization optic 31.

Figure 7:
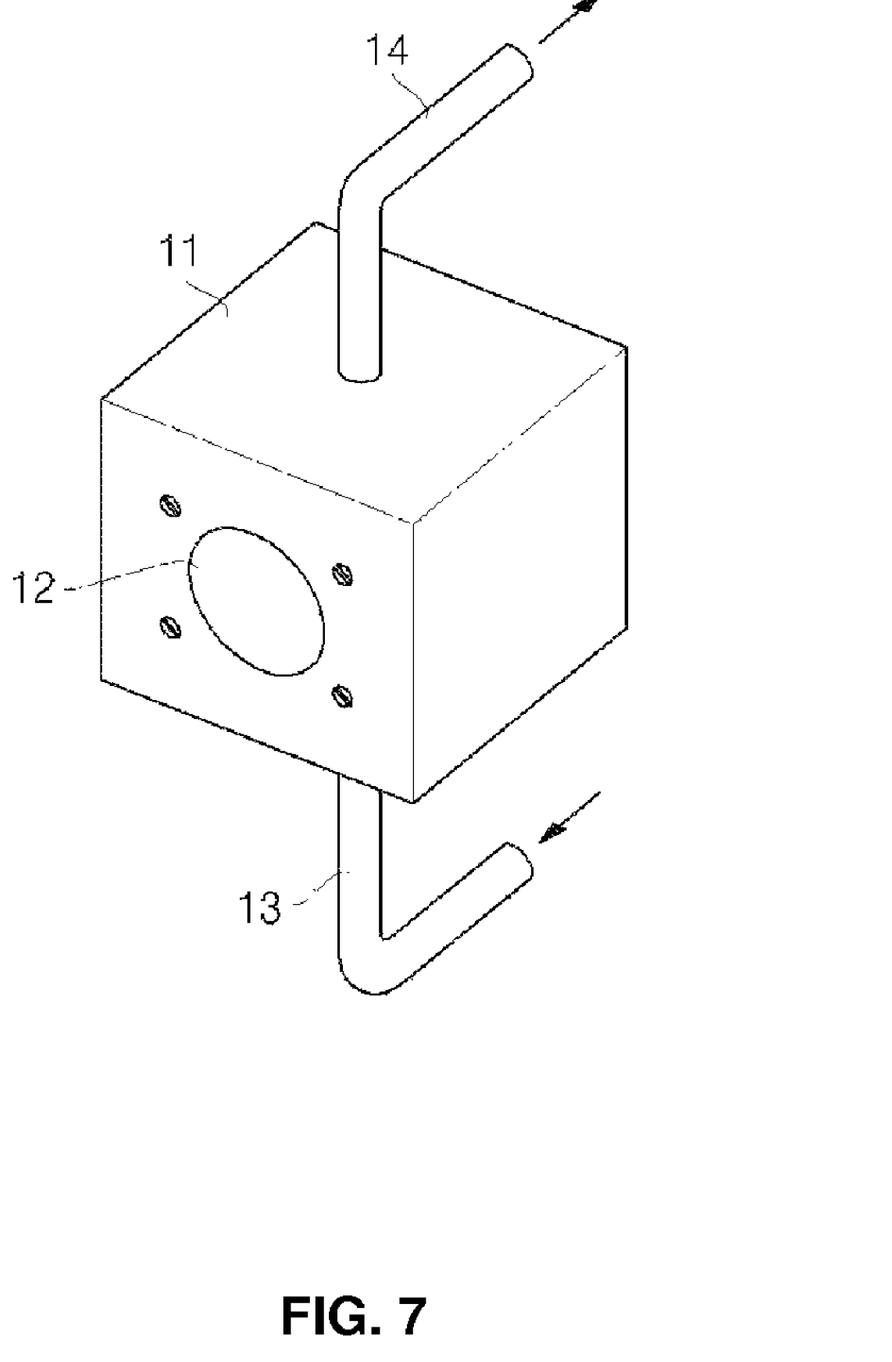
FIG. 7 is a schematic view showing a sample cell of an apparatus for determining a concentration of particulates in water, in accordance with another embodiment of the present invention.

FIG. 7 is a schematic view showing a sample cell of an apparatus for determining a concentration of particulates in water, in accordance with another embodiment of the present invention.

As shown in FIG. 7, the sample cell of the apparatus in accordance with another embodiment of the present invention includes a body 11 having a rectangular shape and storing analyte water as a sample, a transparent optical window 12 formed at one side of the body 11 and transmitting a laser beam, a sample inflow tube 13 through-installed at one end of the body 11 and adapted to introduce fresh water into the body 11, and a sample outflow tube 14 through-installed at one end of the body 11 and discharging water in the body 11 to the outside.

Further, the body 11 is made of a polymer or a metal material.

In a further embodiment of the present invention, the sample cell may be manufactured in the form of an integral structure wherein the body and the cover are not separated and it is therefore possible to reduce production costs.

What is claimed is:

1. An apparatus for measuring a concentration level of impurity particulates in water, comprising:
    a laser beam generator for generating and outputting a laser beam having a predetermined frequency;
    an output control unit for controlling an output of the laser beam, the output control unit including a filter disposed in a laser beam path of the laser beam generator, a motor for rotating the filter, and a controller for controlling an operation of the motor, the filter selected from a variable density filter, a polarization optic, and a wedge optic, the filter capable of adjusting an output intensity of the laser beam upon changing a position by rotation of the motor to control the output of the laser beam to a constant level;
    a beam splitter for splitting a route of the laser beam output through the output control unit into two paths;
    a laser beam measurement unit for measuring the output intensity of the laser beam split from the beam splitter and outputting the measured value as an electrical signal;
    a condensing lens for condensing the laser beam split from the beam splitter;
    a sample cell for storing a water sample and being positioned in the laser beam path to receive irradiation of the condensed laser beam;
    a beam stopper for absorbing the condensed laser beam to prevent an external leakage of light;
    an acoustic sensor coupled to the sample cell, for measuring a sound generated from the sample cell due to collision of the condensed laser beam against impurity particulates in the sample water, and outputting the measured sound value as an electrical signal; and
    a control unit for receiving the electrical signal of the acoustic sensor, calculating a concentration level of impurity particulates in the water sample, and outputting a device control signal to the motor to rotate the filter to a desired position in order to adjust the output intensity of the laser beam.

2. The apparatus according to claim 1, wherein the sample cell includes a body having a rectangular shape for storing the water sample, a cover connected to the upper part of the body and sealing the body, a sample inflow tube installed through the cover and adapted to introduce fresh water into the body, and a sample outflow tube installed through the cover and adapted to discharge the water sample in the body to the outside.

3. The apparatus according to claim 2, wherein the body is made of a transparent optical material capable of transmitting a laser beam while having a high strength so as to withstand high energy of the laser beam, wherein the transparent optical material is selected from the group consisting of BK7, $CaF_2$, $MgF_2$, silica, glass and quartz.

4. The apparatus according to claim 2, wherein the body is configured to have a rectangular structure such that an irradiating laser beam is not refracted or distorted.

5. The apparatus according to claim 2, wherein an upper part of the body is provided with a female screw for engaging with the cover, and a lower part of the cover is provided with a male screw for engaging with the body.

6. The apparatus according to claim 2, wherein the sample inflow tube inside the body is configured to have a longer length than the sample outflow tube.

7. The apparatus according to claim 1, wherein the sample cell includes a body having a rectangular shape for storing the water sample, a transparent optical window formed at one side of the body and transmitting a laser beam, a sample inflow tube installed at one portion of the body and adapted to introduce fresh water into the body, and a sample outflow tube installed at another portion of the body and adapted to discharge the water sample in the body to the outside.

8. The apparatus according to claim 7, wherein the body is made of a material selected from a polymer and a metallic material.

9. The apparatus according to claim 1, wherein the laser beam output from the laser beam generator is output in the form of a pulse having a periodicity of 5 to 30 Hz.

10. The apparatus according to claim 1, wherein the acoustic sensor is installed in a direction perpendicular to an incidence angle of the laser beam.

11. The apparatus according to claim 1, wherein the acoustic sensor is a piezo-electric transducer.

12. The apparatus according to claim 1, wherein the beam stopper is formed of ceramic.

13. The apparatus according to claim 1, wherein the control unit calculates a breakdown ratio (BR) according to the following equation:

BR=Number of Breakdown/Number of Laser Pulses.

14. The apparatus according to claim 13, wherein the control unit calculates a concentration level (Y) from the breakdown ratio (BR) according to the following equation:

$Y=a\times\{BR\}^2+b\times\{BR\}+c$, wherein a, b, and c are a constant.

15. The apparatus according to claim 1, wherein the water sample in the sample cell is introduced at a constant flow rate of 10 to 1000 mL/min.

16. A method for measuring a concentration level of impurity particulates in water, comprising:
providing a water sample;
generating a laser beam;
measuring an energy of the generated laser beam;
determining whether the measured laser beam energy is within the operating condition;
outputting a laser beam pulse when the measured laser beam energy is within the operating condition;
measuring an acoustic signal from the water sample;
filtering a noise from the measured acoustic signal, detecting a breakdown number and then increasing the breakdown number by an increment of +1;
determining whether it reaches a measurement period when the measured laser beam energy is not within the operating condition;
calculating a breakdown ratio (BR) and a concentration level (Y) of particulates when it reaches the measurement period; and
displaying the calculation results on a screen and storing the results in a memory;
wherein the breakdown ratio (BR) is calculated according to the following equation:

BR=Number of Breakdown/Number of Laser Pulses;
and wherein the concentration level (Y) is calculated according to the following equation:
$Y=a\times\{BR\}^2+b\times\{BR\}+c$; in which a, b, and c are a constant.

17. An apparatus for measuring a concentration level of impurity particulates in water, comprising:
a laser beam generator for generating and outputting a laser beam having a predetermined frequency;
an output control unit for controlling an output of the laser beam, the output control unit including a filter disposed in a laser beam path of the laser beam generator, a motor for rotating the filter, and a controller for controlling an operation of the motor, the filter selected from a variable density filter, a polarization optic, and a wedge optic, the filter capable of adjusting an output intensity of the laser beam upon changing a position by rotation of the motor to control the output of the laser beam to a constant level;
a beam splitter for splitting a route of the laser beam output through the output control unit into two paths;
a laser beam measurement unit for measuring the output intensity of the laser beam split from the beam splitter and outputting the measured value as an electrical signal;
a condensing lens for condensing the laser beam split from the beam splitter;
a sample cell for storing a water sample and being positioned in the laser beam path to receive irradiation of the condensed laser beam;
a beam stopper for absorbing the condensed laser beam to prevent an external leakage of light;
an acoustic sensor coupled to the sample cell, for measuring a sound generated from the sample cell due to collision of the condensed laser beam against impurity particulates in the sample water, and outputting the measured sound value as an electrical signal; and
a control unit for receiving the electrical signal of the acoustic sensor, calculating a concentration level of impurity particulates in the water sample, and outputting a device control signal to the motor to rotate the filter to a desired position in order to adjust the output intensity of the laser beam;
wherein the acoustic sensor is installed in a direction perpendicular to an incidence angle of the laser beam;
wherein the control unit calculates a breakdown ratio (BR) according to the following equation:

BR=Number of Breakdown/Number of Laser Pulses.

* * * * *